(12) United States Patent
Govari et al.

(10) Patent No.: US 12,102,382 B2
(45) Date of Patent: Oct. 1, 2024

(54) BIASED ELECTRODES FOR IMPROVED TISSUE CONTACT AND CURRENT DELIVERY

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Justin George Lichter, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 268 days.

(21) Appl. No.: 17/371,008

(22) Filed: Jul. 8, 2021

(65) Prior Publication Data

US 2022/0071696 A1     Mar. 10, 2022

Related U.S. Application Data

(60) Provisional application No. 63/076,614, filed on Sep. 10, 2020.

(51) Int. Cl.
*A61B 18/14* (2006.01)
*A61B 17/00* (2006.01)
(Continued)

(52) U.S. Cl.
CPC ............ *A61B 18/1492* (2013.01); *A61B 2017/00185* (2013.01); *A61B 2018/00077* (2013.01);
(Continued)

(58) Field of Classification Search
CPC ...... A61B 18/1492; A61B 2017/00185; A61B 2018/00077; A61B 2018/00136;
(Continued)

(56) References Cited

U.S. PATENT DOCUMENTS 3,359,525 A   12/1967   Hubbach
4,699,147 A   10/1987   Chilson et al.
(Continued)

FOREIGN PATENT DOCUMENTS

CN   111248993 A   6/2020
CN   111248996 A   6/2020
(Continued)

OTHER PUBLICATIONS

Ron Robinette, Swiss Machining of Medical Electrodes Made from MP35N(R), Jun. 23, 2020, Metal Cutting Corporation (Year: 2020).*
(Continued)

*Primary Examiner* — Linda C Dvorak
*Assistant Examiner* — Abigail Bock
(74) *Attorney, Agent, or Firm* — Troutman Pepper Hamilton Sanders LLP

(57) ABSTRACT

A medical probe, including a flexible insertion tube having proximal and distal ends, and a basket assembly at the distal end of the flexible insertion tube. In embodiments of the present invention, the basket assembly includes a plurality of spines and a plurality of electrodes, each of the electrodes having a lumen therethrough fitting a given spine.

10 Claims, 5 Drawing Sheets

(51) Int. Cl.
*A61B 18/00* (2006.01)
*A61B 18/12* (2006.01)
*A61M 25/00* (2006.01)

(52) U.S. Cl.
CPC ............... *A61B 2018/00136* (2013.01); *A61B 2018/00178* (2013.01); *A61B 2018/00267* (2013.01); *A61B 2018/00357* (2013.01); *A61B 2018/00577* (2013.01); *A61B 2018/00601* (2013.01); *A61B 2018/00613* (2013.01); *A61B 2018/00761* (2013.01); *A61B 2018/1253* (2013.01); *A61B 2018/126* (2013.01); *A61B 2018/144* (2013.01); *A61B 2018/1467* (2013.01); *A61B 2218/002* (2013.01); *A61M 2025/0079* (2013.01)

(58) Field of Classification Search
CPC ........... A61B 2018/00178; A61B 2018/00267; A61B 2018/00357; A61B 2018/00577; A61B 2018/00601; A61B 2018/00613; A61B 2018/00761; A61B 2018/1253; A61B 2018/126; A61B 2018/144; A61B 2018/1497; A61B 2218/002; A61M 2025/0079
See application file for complete search history.

(56) References Cited

U.S. PATENT DOCUMENTS

| | | | |
|---|---|---|---|
| 4,940,064 | A | 7/1990 | Desai |
| 5,215,103 | A | 6/1993 | Desai |
| 5,255,679 | A | 10/1993 | Imran |
| 5,293,869 | A | 3/1994 | Edwards et al. |
| 5,309,910 | A | 5/1994 | Edwards et al. |
| 5,313,943 | A | 5/1994 | Houser et al. |
| 5,324,284 | A | 6/1994 | Imran |
| 5,345,936 | A | 9/1994 | Pomeranz et al. |
| 5,365,926 | A | 11/1994 | Desai |
| 5,391,199 | A | 2/1995 | Ben-Haim |
| 5,396,887 | A | 3/1995 | Imran |
| 5,400,783 | A | 3/1995 | Pomeranz et al. |
| 5,411,025 | A | 5/1995 | Webster, Jr. |
| 5,415,166 | A | 5/1995 | Imran |
| 5,456,254 | A | 10/1995 | Pietroski et al. |
| 5,465,717 | A | 11/1995 | Imran et al. |
| 5,476,495 | A | 12/1995 | Kordis et al. |
| 5,499,981 | A | 3/1996 | Kordis |
| 5,526,810 | A | 6/1996 | Wang |
| 5,546,940 | A | 8/1996 | Panescu et al. |
| 5,549,108 | A | 8/1996 | Edwards et al. |
| 5,558,073 | A | 9/1996 | Pomeranz et al. |
| 5,577,509 | A | 11/1996 | Panescu et al. |
| 5,595,183 | A | 1/1997 | Swanson et al. |
| 5,598,848 | A | 2/1997 | Swanson et al. |
| 5,609,157 | A | 3/1997 | Panescu et al. |
| 5,628,313 | A | 5/1997 | Webster, Jr. |
| 5,681,280 | A | 10/1997 | Rusk et al. |
| 5,722,401 | A | 3/1998 | Pietroski et al. |
| 5,722,403 | A | 3/1998 | McGee et al. |
| 5,725,525 | A | 3/1998 | Kordis |
| 5,730,128 | A | 3/1998 | Pomeranz et al. |
| 5,772,590 | A | 6/1998 | Webster, Jr. |
| 5,782,899 | A | 7/1998 | Imran |
| 5,823,189 | A | 10/1998 | Kordis |
| 5,862,030 | A | 1/1999 | Watkins, Jr. et al. |
| 5,881,727 | A | 3/1999 | Edwards |
| 5,893,847 | A | 4/1999 | Kordis |
| 5,904,680 | A | 5/1999 | Kordis et al. |
| 5,911,739 | A | 6/1999 | Kordis et al. |
| 5,928,228 | A | 7/1999 | Kordis et al. |
| 5,944,022 | A | 8/1999 | Nardella et al. |
| 5,968,040 | A | 10/1999 | Swanson et al. |
| 5,983,126 | A | 11/1999 | Wittkampf |
| 6,014,579 | A | 1/2000 | Pomeranz et al. |
| 6,014,590 | A | 1/2000 | Whayne et al. |
| 6,119,030 | A | 9/2000 | Morency |
| 6,142,993 | A | 11/2000 | Whayne et al. |
| 6,216,043 | B1 | 4/2001 | Swanson et al. |
| 6,216,044 | B1 | 4/2001 | Kordis |
| 6,239,724 | B1 | 5/2001 | Doron et al. |
| 6,332,089 | B1 | 12/2001 | Acker et al. |
| 6,428,537 | B1 | 8/2002 | Swanson et al. |
| 6,456,864 | B1 | 9/2002 | Swanson et al. |
| 6,484,118 | B1 | 11/2002 | Govari |
| 6,569,162 | B2 | 5/2003 | He et al. |
| 6,574,492 | B1 | 6/2003 | Ben-Haim et al. |
| 6,582,429 | B2 | 6/2003 | Krishnan et al. |
| 6,584,345 | B2 | 6/2003 | Govari |
| 6,600,948 | B2 | 7/2003 | Ben-Haim et al. |
| 6,618,612 | B1 | 9/2003 | Acker et al. |
| 6,690,963 | B2 | 2/2004 | Ben-Haim et al. |
| 6,738,655 | B1 | 5/2004 | Sen et al. |
| 6,741,878 | B2 | 5/2004 | Fuimaono et al. |
| 6,748,255 | B2 | 6/2004 | Fuimaono et al. |
| 6,780,183 | B2 | 8/2004 | Jimenez, Jr. et al. |
| 6,837,886 | B2 | 1/2005 | Collins et al. |
| 6,866,662 | B2 | 3/2005 | Fuimaono et al. |
| 6,892,091 | B1 | 5/2005 | Ben-Haim et al. |
| 6,970,730 | B2 | 11/2005 | Fuimaono et al. |
| 6,973,340 | B2 | 12/2005 | Fuimaono et al. |
| 6,980,858 | B2 | 12/2005 | Fuimaono et al. |
| 7,048,734 | B1 | 5/2006 | Fleischman et al. |
| 7,149,563 | B2 | 12/2006 | Fuimaono et al. |
| 7,255,695 | B2 | 8/2007 | Falwell et al. |
| 7,257,434 | B2 | 8/2007 | Fuimaono et al. |
| 7,399,299 | B2 | 7/2008 | Daniel et al. |
| 7,410,486 | B2 | 8/2008 | Fuimaono et al. |
| 7,522,950 | B2 | 4/2009 | Fuimaono et al. |
| RE41,334 | E | 5/2010 | Beatty et al. |
| 7,846,157 | B2 | 12/2010 | Kozel |
| 7,850,685 | B2* | 12/2010 | Kunis ................ A61B 18/1492 606/41 |
| 7,930,018 | B2 | 4/2011 | Harlev et al. |
| 8,007,495 | B2 | 8/2011 | McDaniel et al. |
| 8,048,063 | B2 | 11/2011 | Aeby et al. |
| 8,103,327 | B2 | 1/2012 | Harlev et al. |
| 8,167,845 | B2 | 5/2012 | Wang et al. |
| 8,224,416 | B2 | 7/2012 | De La Rama et al. |
| 8,235,988 | B2 | 8/2012 | Davis et al. |
| 8,346,339 | B2 | 1/2013 | Kordis et al. |
| 8,435,232 | B2 | 5/2013 | Aeby et al. |
| 8,447,377 | B2 | 5/2013 | Harlev et al. |
| 8,475,450 | B2* | 7/2013 | Govari ................ A61B 18/1492 606/41 |
| 8,498,686 | B2 | 7/2013 | Grunewald |
| 8,517,999 | B2 | 8/2013 | Pappone et al. |
| 8,545,490 | B2 | 10/2013 | Mihajlovic et al. |
| 8,560,086 | B2 | 10/2013 | Just et al. |
| 8,567,265 | B2 | 10/2013 | Aeby et al. |
| 8,712,550 | B2 | 4/2014 | Grunewald |
| 8,755,861 | B2 | 6/2014 | Harlev et al. |
| 8,825,130 | B2 | 9/2014 | Just et al. |
| 8,906,011 | B2 | 12/2014 | Gelbart et al. |
| 8,945,120 | B2 | 2/2015 | McDaniel et al. |
| 8,979,839 | B2 | 3/2015 | De La Rama et al. |
| 9,037,264 | B2 | 5/2015 | Just et al. |
| 9,044,232 | B2 | 6/2015 | Cheng et al. |
| 9,131,980 | B2 | 9/2015 | Bloom |
| 9,204,929 | B2 | 12/2015 | Solis |
| 9,277,960 | B2 | 3/2016 | Weinkam et al. |
| 9,314,208 | B1 | 4/2016 | Altmann et al. |
| 9,339,331 | B2 | 5/2016 | Tegg et al. |
| 9,486,282 | B2 | 11/2016 | Solis |
| 9,554,718 | B2 | 1/2017 | Bar-Tal et al. |
| D782,686 | S | 3/2017 | Werneth et al. |
| 9,585,588 | B2 | 3/2017 | Marecki et al. |
| 9,597,036 | B2 | 3/2017 | Aeby et al. |
| 9,687,297 | B2 | 6/2017 | Just et al. |
| 9,693,733 | B2 | 7/2017 | Altmann et al. |
| 9,782,099 | B2 | 10/2017 | Williams et al. |
| 9,788,895 | B2 | 10/2017 | Solis |
| 9,801,681 | B2 | 10/2017 | Laske et al. |

(56) References Cited

U.S. PATENT DOCUMENTS

| | | |
|---|---|---|
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0125772 A1 | 5/2008 | Stone et al. |
| 2008/0234564 A1 | 9/2008 | Beatty et al. |
| 2009/0149848 A1 | 6/2009 | Werneth et al. |
| 2009/0171274 A1 | 7/2009 | Harlev et al. |
| 2011/0118726 A1 | 5/2011 | De La Rama et al. |
| 2011/0137298 A1 | 6/2011 | Nguyen et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2012/0067640 A1 | 3/2012 | Moulin et al. |
| 2012/0271136 A1 | 10/2012 | Kordis et al. |
| 2013/0090651 A1 | 4/2013 | Smith |
| 2013/0131661 A1 | 5/2013 | Jackson et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0282084 A1 | 10/2013 | Mathur et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276124 A1 | 9/2014 | Cholette et al. |
| 2014/0276712 A1 | 9/2014 | Mallin et al. |
| 2014/0276733 A1 | 9/2014 | Van Scoy et al. |
| 2014/0276789 A1 | 9/2014 | Dandler et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0157382 A1 | 6/2015 | Avitall et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0272654 A1 | 10/2015 | Esch et al. |
| 2015/0342532 A1 | 12/2015 | Basu et al. |
| 2015/0366508 A1 | 12/2015 | Chou et al. |
| 2016/0073960 A1 | 3/2016 | Jung et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |

(56) References Cited

U.S. PATENT DOCUMENTS

| | | |
|---|---|---|
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0164858 A1 | 6/2017 | Basu |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0042674 A1 | 2/2018 | Mickelsen |
| 2018/0049803 A1 | 2/2018 | Solis |
| 2018/0056038 A1* | 3/2018 | Aujla ............... A61M 25/0082 |
| 2018/0085064 A1 | 3/2018 | Auerbach et al. |
| 2018/0092688 A1 | 4/2018 | Tegg |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0214202 A1 | 8/2018 | Howard et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0353238 A1* | 12/2018 | Schultz ............... A61B 1/0052 |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0282116 A1 | 9/2019 | Olson |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0107879 A1 | 4/2020 | Stewart et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0163707 A1 | 5/2020 | Sliwa et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2020/0398050 A1 | 12/2020 | Viswanathan et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0153932 A1 | 5/2021 | Voth et al. |
| 2021/0161592 A1 | 6/2021 | Altman et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |

(56) References Cited

U.S. PATENT DOCUMENTS

| | | |
|---|---|---|
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |
| 2022/0071695 A1 | 3/2022 | Beeckler et al. |
| 2022/0304745 A1 | 9/2022 | Olson |

FOREIGN PATENT DOCUMENTS

| | | | |
|---|---|---|---|
| CN | 111728693 A | 10/2020 | |
| EP | 0668740 A1 | 8/1995 | |
| EP | 0879613 A2 * | 11/1998 | ............ A61M 25/01 |
| EP | 0644738 B1 | 3/2000 | |
| EP | 0727183 B1 | 11/2002 | |
| EP | 0727184 B1 | 12/2002 | |
| EP | 2783651 A1 | 10/2014 | |
| EP | 2699151 B1 | 11/2015 | |
| EP | 2699152 B1 | 11/2015 | |
| EP | 2699153 B1 | 12/2015 | |
| EP | 2954868 A1 | 12/2015 | |
| EP | 2498706 B1 | 4/2016 | |
| EP | 2578173 B1 | 6/2017 | |
| EP | 3181082 A1 * | 6/2017 | ......... A61B 18/1492 |
| EP | 3238645 A1 | 11/2017 | |
| EP | 2884931 B1 | 1/2018 | |
| EP | 2349440 B1 | 8/2019 | |
| EP | 3318211 B1 | 12/2019 | |
| EP | 3581135 A1 | 12/2019 | |
| EP | 2736434 B1 | 2/2020 | |
| EP | 3451962 B1 | 3/2020 | |
| EP | 3967253 A2 | 3/2022 | |
| EP | 3972510 A1 | 3/2022 | |
| EP | 3991681 A1 | 5/2022 | |
| WO | 9421167 A1 | 9/1994 | |
| WO | 9421169 A1 | 9/1994 | |
| WO | 1996/005768 A1 | 2/1996 | |
| WO | 9625095 A1 | 8/1996 | |
| WO | 9634560 A1 | 11/1996 | |
| WO | 0182814 B1 | 5/2002 | |
| WO | 2004087249 A2 | 10/2004 | |
| WO | 2012100185 A2 | 7/2012 | |
| WO | 2013052852 A1 | 4/2013 | |
| WO | 2013162884 A1 | 10/2013 | |
| WO | 2013173917 A1 | 11/2013 | |
| WO | 2013176881 A1 | 11/2013 | |
| WO | 2014/124231 A1 | 8/2014 | |
| WO | 2014/158708 A1 | 10/2014 | |
| WO | 2014176205 A1 | 10/2014 | |
| WO | 2016019760 A1 | 2/2016 | |
| WO | 2016044687 A1 | 3/2016 | |
| WO | WO-2016075544 A2 * | 5/2016 | ......... A61B 18/0206 |
| WO | 2016/130713 A1 | 8/2016 | |
| WO | 2018111600 A1 | 6/2018 | |
| WO | 2018191149 A1 | 10/2018 | |
| WO | 2019084442 A1 | 5/2019 | |
| WO | 2019143960 A1 | 7/2019 | |
| WO | WO-2019177809 A1 * | 9/2019 | ......... A61B 18/1492 |
| WO | 2020026217 A1 | 2/2020 | |
| WO | 2020206328 A1 | 10/2020 | |
| WO | 2020251857 A1 | 12/2020 | |
| WO | 2022020591 A1 | 1/2022 | |

OTHER PUBLICATIONS

Extended European Search Report dated Dec. 2, 2022, from corresponding European Appl. No. 22183542.4.
Partial European Search Report dated Jan. 26, 2022, from corresponding European Appl. No. 21195668.5.
Extended European Search Report dated Jun. 1, 2022, from corresponding European Appl. No. 21195668.5.
Extended European Search Report dated Mar. 23, 2022, from European Application No. 21204799.7.
picwire.com, "Interconnect Solutions, 50 OHM RF Cable Solutions", https://picwire.com/cables/50Ohm-Coax-Triax (Year: 2020).
Extended European Search Report dated Sep. 23, 2022, from corresponding European Application No. 22168805.4.

* cited by examiner

BIASED ELECTRODES FOR IMPROVED TISSUE CONTACT AND CURRENT DELIVERY

CROSS-REFERENCE TO RELATED APPLICATION

This application claims the benefit of U.S. Provisional Patent Application 63/076,614, filed 10 Sep. 2020, which is incorporated herein by reference.

FIELD OF THE INVENTION

The present invention relates generally to medical probes, and specifically to fabricating biased electrodes for a basket catheter.

BACKGROUND OF THE INVENTION

Arrhythmias are abnormal heart rhythms that are typically caused by a small area of cardiac tissue that produces irregular heartbeats. Cardiac ablation is a medical procedure that can be performed to treat an arrhythmia by destroying the area of the cardiac tissue causing the irregular heartbeats. Some medical systems use irreversible electroporation (IRE) to ablate cardiac tissue. IRE is a nonthermal ablation method based on the unrecoverable permeabilization of cell membranes caused by short pulses of high voltage delivered to the tissue.

U.S. Patent Application 2013/0282084 to Mathur et al., describes an apparatus for treatment of in-stent restenosis. The apparatus includes an elongate flexible catheter body with a radially expandable structure comprising a plurality of electrodes or other electrosurgical energy delivery surfaces to engage tissue when the structure expands. The electrodes may be fabricated as part of struts that form a basket. In some embodiments, the electrodes can be wider than the struts.

U.S. Pat. No. 6,569,162 to He describes a design for a passively self-cooled ablation electrode. The electrode includes a greater surface area that allows electrode to dissipate heat to the blood pool more effectively and increased thermal mass, thereby improving heat transfer between the electrode and tissue for more controlled heating and ablation of the tissue. The electrode comprises a substantially solid electrode body with thick walls that results in increased thermal mass and thermal conductivity. In one embodiment, the electrode may have a substantially curved exterior surface at the distal end of the electrode body, for use a tip electrode, or a central lumen extending through the electrode body, for use a ring electrode. In another embodiment, the plurality of projections integrally formed within the exterior surface of the electrode extend substantially parallel to the axis of the electrode to form a plurality of axial fins.

U.S. Pat. No. 6,582,429 to Krishnan et al., describes a design for an ablation catheter with covered electrodes. The catheter includes a shaft having a curved distal-end region with an inner surface and an outer surface and a plurality of band electrodes positioned at the distal end of the shaft. The configuration of the electrodes may comprise twelve band electrodes arranged in a substantially linear array along the distal segment of the catheter sheath. In some embodiments, the electrodes may comprise a tip electrode.

U.S. Pat. No. 8,475,450 to Govari et al., describes a dual-purpose lasso catheter with irrigation. The lasso catheter includes electrodes that that bulge above the outer surface of the electrodes in order to increase the surface area that is in contact with heart tissue, and thus reduce the electrical resistance when the electrodes are used for ablation.

The description above is presented as a general overview of related art in this field and should not be construed as an admission that any of the information it contains constitutes prior art against the present patent application.

SUMMARY OF THE INVENTION

There is provided, in accordance with an embodiment of the present invention, a surgical imaging system, including a flexible insertion tube having proximal and distal ends, a basket assembly at the distal end of the flexible insertion tube, the basket assembly including a plurality of spines, and a plurality of electrodes, each of the electrodes having a lumen therethrough fitting a given spine.

In one embodiment, the spines have respective outer sides and inner sides, and each given electrode includes a conductive material biased towards the outer side of is respective spine.

In another embodiment, the spines have respective outer sides and inner sides, and each given electrode also has a notch between the lumen and the inner side of its respective spine.

In some embodiments, each given spine includes a wire affixed to the inner side of the given spine, and the notch includes solder material forming an electrical connection between the each given electrode and the wire.

In an additional embodiment, the surgical imaging system also includes an adhesive material applied to an inner surface of each given electrode, and the inner surface is defined by the lumen of the each given electrode.

In a further embodiment, each of the electrodes has one or more smoothed edges.

In a supplemental embodiment, the medical probe also includes a set of spray ports configured to deliver an irrigation fluid to the electrodes.

In another embodiment, the medical probe also includes a set of spray ports configured to deliver an irrigation fluid between the spines.

There is also provided, in accordance with an embodiment of the present invention, a method including providing a medical probe having a plurality of spines, providing an extruded tube of a conductive material, performing a cutting operation on the extruded tube so as to form an electrode body, and fitting the formed electrode body around a given spine.

In one embodiment, the plurality of spines forms a basket assembly at a distal end of the medical probe.

In another embodiment, the cutting operation forms sharp edges on the electrode body, and the method also includes smoothing out the sharp edges.

In an additional embodiment, the extruded tube defines a lumen, wherein the tube is not radially symmetric about the lumen.

In a further embodiment, the given spine has an outer side and an inner side, wherein fitting the formed electrode body on the given spine includes biasing the electrode body towards the outer side of the given spine.

In a supplemental embodiment, the given spine has an outer side and an inner side, wherein the cutting operation includes cutting a notch between the lumen and the inner side of the given spine.

In some embodiments, the given spine includes a wire affixed to the inner side of the given spine, and the method also includes filling the notch with solder so as to form an electrical connection between the wire and the electrode body.

In an additional embodiment, fitting the formed electrode body around the given spine includes forming an adhesive bond between the electrode body and the given spine.

In a further embodiment, the method also includes providing a set of spray ports configured to deliver an irrigation fluid to the electrodes.

In another embodiment, the method also includes providing a set of spray ports configured to deliver an irrigation fluid between the spines.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

To deliver pulsed field ablation (PFA) in an IRE (irreversible electroporation) procedure, electrodes should contact the tissue being ablated with as large a surface area as possible. Embodiments of the present invention provide a medical probe with a basket assembly comprising electrodes that are biased in cross section so that there is more material on the tissue contacting side, while minimizing unnecessary material on the non-tissue contacting side. As described hereinbelow, the medical probe includes a flexible insertion tube having proximal and distal ends, and a basket assembly at the distal end of the flexible insertion tube. The basket assembly comprises a plurality of spines and a plurality of electrodes, each given electrode having a lumen therethrough fitting a given spine.

Biasing the electrodes so that there is more material on the tissue contacting side allows the basket assembly of a medical probe implementing embodiments of the present invention to collapse into a small sheath. Another aspect of this electrode design ensures that the bias (i.e., the protrusion) is atraumatic. In some embodiments, the atraumaticity is implemented by smoothing out any sharp edges in the electrodes. Smoothing out sharp edges prevents any damage to tissue or the sheath, and helps prevent high current density that may result in arcing.

System Description

Figure 1:
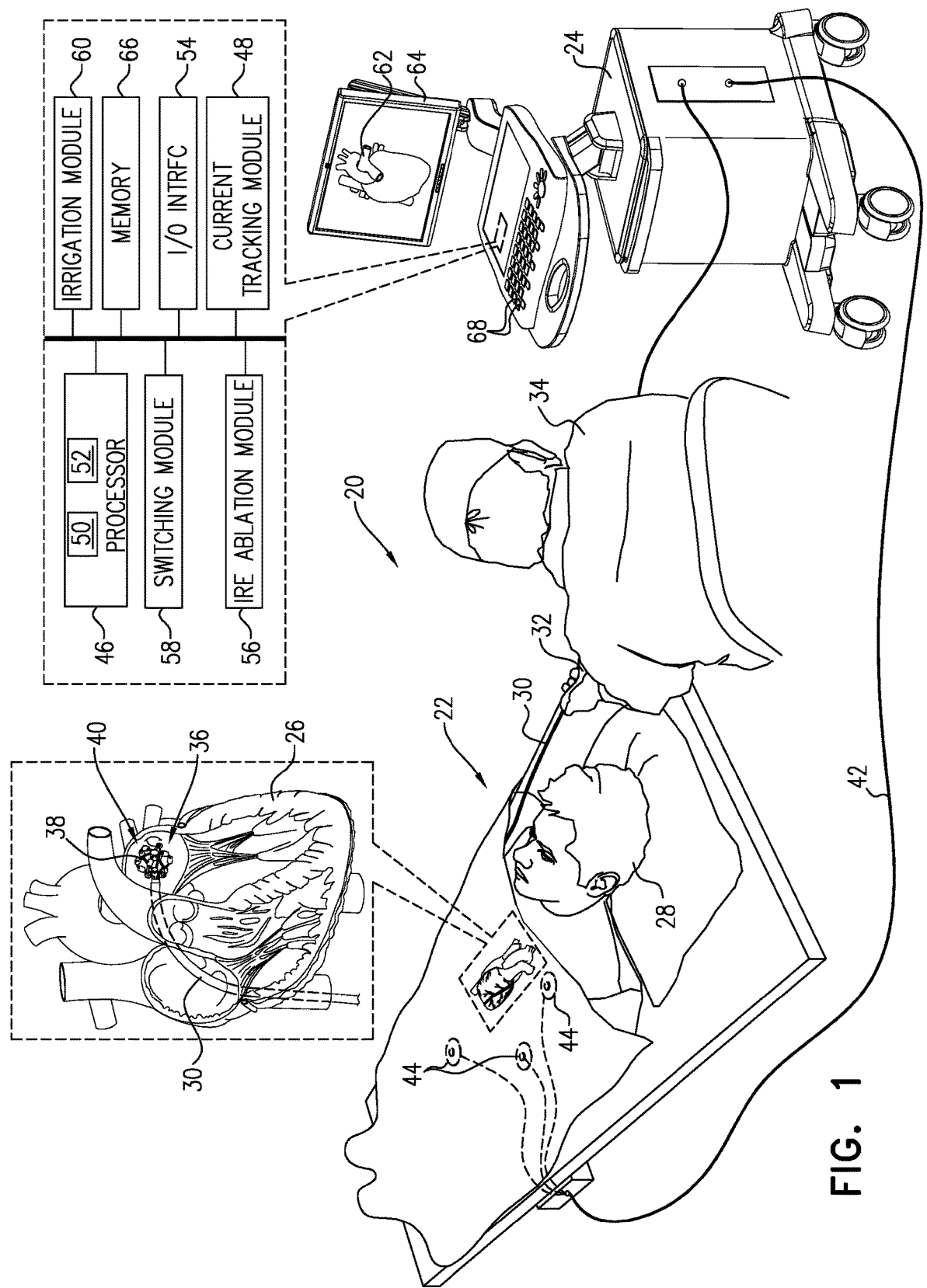
FIG. 1 is a schematic pictorial illustration of a medical system 20 comprising a medical probe whose distal end comprises a basket assembly with biased electrodes, in accordance with an embodiment of the present invention.

FIG. 1 is a schematic, pictorial illustration of a medical system 20 comprising a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Probe 22 comprises a flexible insertion tube 30 and a handle coupled to a proximal end of the insertion tube. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy a basket assembly 38 affixed to distal end 36. Basket assembly 38 comprises a set of electrodes 40 (also referred to herein as electrode bodies 40) affixed to a plurality of spines, as described in the description referencing FIGS. 3, 6 and 7 hereinbelow.

To start performing a medical procedure such as irreversible electroporation (IRE) ablation, medical professional 34 can manipulate handle 32 to position distal end 36 so that electrodes 40 engage cardiac tissue at a desired location or locations.

In the configuration shown in FIG. 1, control console 24 is connected, by a cable 42, to body surface electrodes, which typically comprise adhesive skin patches 44 that are affixed to patient 28. Control console 24 comprises a processor 46 that, in conjunction with a current tracking module 48, determines location coordinates of distal end 36 inside heart 26 based on impedances and/or currents measured between adhesive skin patches 44 and electrodes 40 that are affixed to basket assembly 38. In addition to being used as location sensors during a medical procedure, electrodes 40 may perform other tasks such as ablating tissue in the heart.

As described hereinabove, in conjunction with current tracking module 48, processor 46 may determine location coordinates of distal end 36 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are (also) configured to deliver IRE ablation energy to tissue in heart 26, configuring electrodes 40 to deliver any other type of ablation energy to tissue in any body cavity is considered to be within the spirit and scope of the present invention.

Processor 46 may comprise real-time noise reduction circuitry 50 typically configured as a field programmable gate array (FPGA), followed by an analog-to-digital (A/D) signal conversion integrated circuit 52. The processor can be programmed to perform one or more algorithms disclosed herein, each of the one or more algorithms comprising steps described hereinbelow. The processor uses circuitry 50 and circuit 52 as well as features of modules which are described in more detail below, in order to perform the one or more algorithms.

Although the medical system shown in FIG. 1 uses impedance or current-based sensing to measure a location of distal end 36, other location tracking techniques may be used (e.g., techniques using magnetic-based sensors). Impedance and current-based location tracking techniques are described, for example, in U.S. Pat. Nos. 5,983,126, 6,456, 864 and 5,944,022. The methods of location sensing described hereinabove are implemented in the above-mentioned CARTO® system and are described in detail in the patents cited above.

Control console 24 also comprises an input/output (I/O) communications interface 54 that enables control console 24 to transfer signals from, and/or transfer signals to electrodes 40 and adhesive skin patches 44. In the configuration shown in FIG. 1, control console 24 additionally comprises an IRE ablation module 56 and a switching module 58.

IRE ablation module 56 is configured to generate IRE pulses comprising peak power in the range of tens of kilowatts. As described hereinbelow, medical system 20 performs IRE ablation by delivering IRE pulses to pairs of electrodes 40. In some embodiments, a given pair of the electrodes comprises two sets of electrodes 40 with each of the sets having at least one electrode 40. Using switching module 58, IRE ablation module 56 can deliver one or more IRE pulses independently to each of the pairs of the electrodes.

In order to dissipate the heat and to improve the efficiency of the ablation process, system 20 supplies irrigation fluid (e.g., a saline solution) to distal end 36 via a channel (not shown) in insertion tube 30. Control console 24 comprises an irrigation module 60 to monitor and control irrigation parameters, such as the pressure and the temperature of the irrigation fluid.

Based on signals received from electrodes 40 and/or adhesive skin patches 44, processor 46 can generate an electroanatomical map 62 that shows the location of distal end 36 in the patient's body. During the procedure, processor 46 can present map 62 to medical professional 34 on a display 64, and store data representing the electroanatomical map in a memory 66. Memory 66 may comprise any suitable volatile and/or non-volatile memory, such as random-access memory or a hard disk drive.

In some embodiments, medical professional 34 can manipulate map 62 using one or more input devices 68. In alternative embodiments, display 64 may comprise a touch-screen that can be configured to accept inputs from medical professional 34, in addition to presenting map 62.

Figure 2:
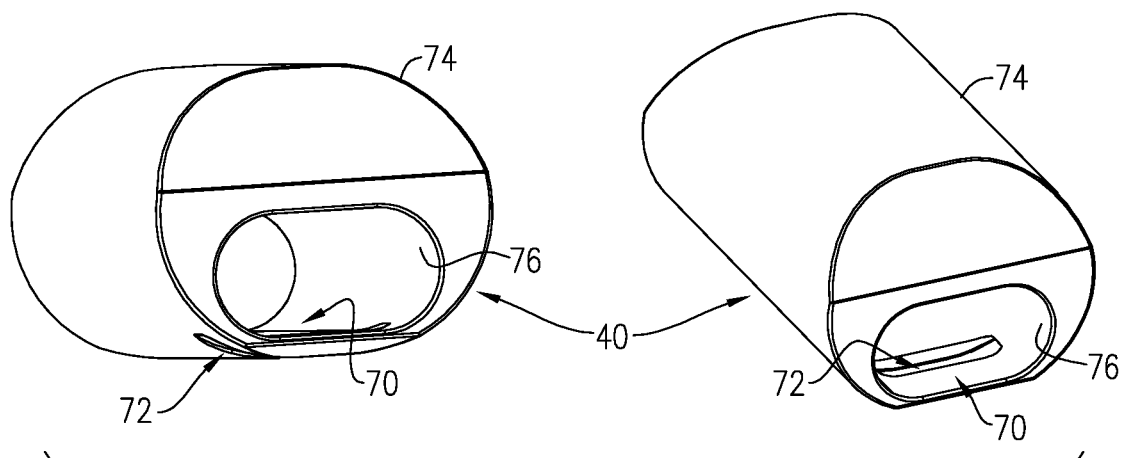
FIG. 2 is a schematic pictorial illustration showing angled views of a given biased electrode, in accordance with an embodiment of the present invention.

FIG. 2 is a schematic pictorial illustration showing angled views of a given electrode 40, in accordance with an embodiment of the present invention. Each electrode 40 is fabricated from a biocompatible electrically conductive material, has an electrode lumen 70 therethrough, and has a notch 72 that extends from an outer surface 74 of the electrode to the lumen. In addition to outer surface 74, each given electrode 40 has an inner surface 76 defined by its respective lumen 70.

Figure 3A:
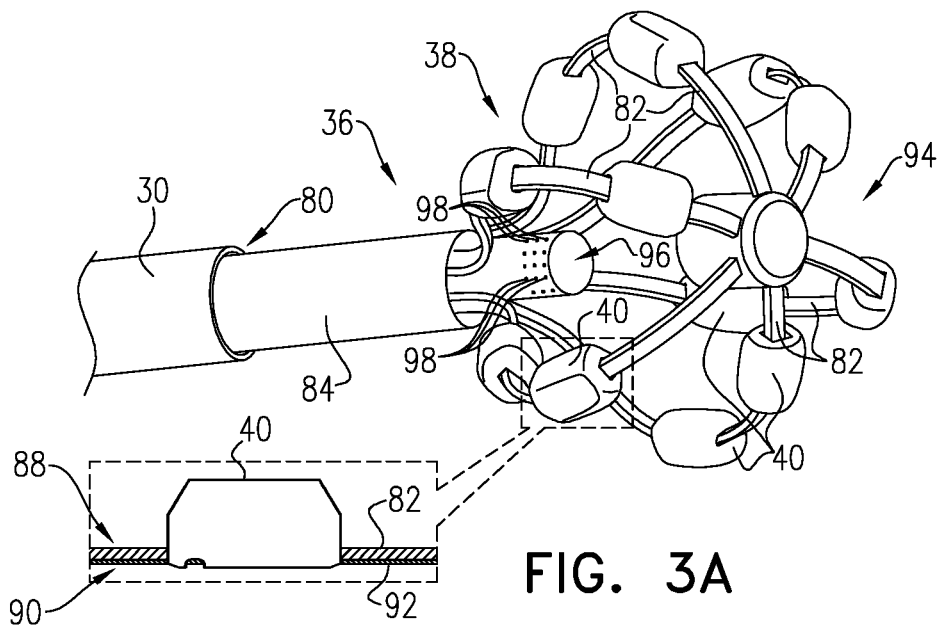
FIGS. 3A and 3B, also referred to herein collectively as FIG. 3 are schematic pictorial illustrations of the distal end of the medical probe, in accordance with an embodiment of the present invention.
Figure 3B:
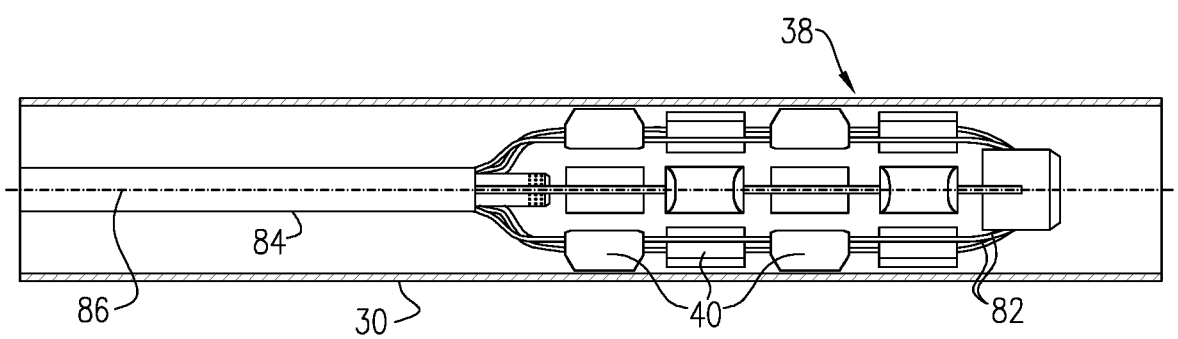

FIGS. 3A and 3B, also referred to herein collectively as FIG. 3, are schematic pictorial illustrations of distal end 36 comprising basket assembly 38, in accordance with an embodiment of the present invention. FIG. 3A shows basket assembly 38 in an expanded configuration when unconstrained, such as by being advanced out of an insertion tube lumen 80 at distal end 36, and FIG. 3B shows the basket assembly in a collapsed configuration within insertion tube 30. As shown in FIG. 3B, the outward bias of electrodes 40 enable spines 82 to lay flush with shaft 84 when basket assembly 38 is collapsed within insertion tube 30.

By way of example, as shown in FIG. 3A, basket assembly 38 comprises a plurality of flexible spines 82 that are formed at the end of a tubular shaft 84 and are connected at their proximal and distal ends. During a medical procedure, medical professional 34 can deploy basket assembly 38 by extending tubular shaft 84 from insertion tube 30. Spines 82 may have elliptical (e.g., circular) or rectangular (that may appear to be flat) cross-sections, and typically comprise a flexible, resilient material (e.g., a shape-memory alloy such nickel-titanium, also known as Nitinol). In its expanded configuration, basket assembly 38 has an expanded arrangement (FIG. 3A) wherein spines 82 bow radially outwardly and a collapsed arrangement (FIG. 3B) wherein the spines are arranged generally along a longitudinal axis 86 of insertion tube 30.

In the configuration shown in FIG. 3, one or more electrodes are threaded on to each given spine 82 so as to fit the electrodes to the spines. Fitting a given electrode 40 to a given spine 82 is described in the description referencing FIGS. 6 and 7 hereinbelow.

In embodiments described herein, electrodes 40 can be configured to deliver ablation energy to tissue in heart 26. In addition to using electrodes 40 to deliver ablation energy, the electrodes can also be used to determine the location of basket assembly 38 and/or to measure a physiological property such as local surface electrical potentials at respective locations on tissue in heart 26.

Each spine 82 has an outer side 88 and an inner side 90. In embodiments of the present invention, for a given electrode 40 fitted to a given spine 82, the given spine is planar at the given electrode, wherein the plane divides the given electrode asymmetrically so that there is more conductive material on the outer side (of the plane) than on the inner side. In these embodiments, electrodes 40 (i.e., when fitted to spines 82) are biased towards the outer sides of the spines 82, as there is a greater surface area of the given electrode on the outer side compared to the surface area of the given electrode on the inner side.

Examples of materials ideally suited for forming electrodes include gold, platinum and palladium (and their respective alloys). These materials also have very high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 26.

Probe 22 also comprises a set of wires 92 that couple IRE ablation module 56 to electrodes 40. In some embodiments each spine comprises a given wire 92 affixed to its inner side 90. Connecting wires 92 to electrodes 40 is described in the description referencing FIG. 7 hereinbelow.

Basket assembly 38 has a distal end 94 and comprises a stem that extends longitudinally from a distal end of shaft 84 towards distal end 94. As described supra, control console 24 comprises irrigation module 60 that delivers irrigation fluid to distal end 36. Stem 96 comprises multiple spray ports 98, wherein each given spray port 98 is angled to aim delivery of the irrigation fluid to either a given electrode 40 or to tissue in heart 26 (i.e., by aiming the delivery between two adjacent spines 82).

By biasing electrodes 40 to outer side 88, the electrodes deliver more ablation energy from the portion of the electrodes outer side of the spines (i.e., significantly more than the ablation energy delivered from the portion of the electrodes on the inner side of the spines). Since electrodes 40 do not comprise spray ports that deliver irrigation fluid, the configuration described hereinabove enables heat to be transferred from the tissue (i.e., during an ablation procedure) to the portion of the electrodes on the inner side of the spines, and the electrodes can be cooled by aiming the irrigation fluid, via spray ports 98, at the portion of the electrodes on the inner side of the spines.

Figure 4:
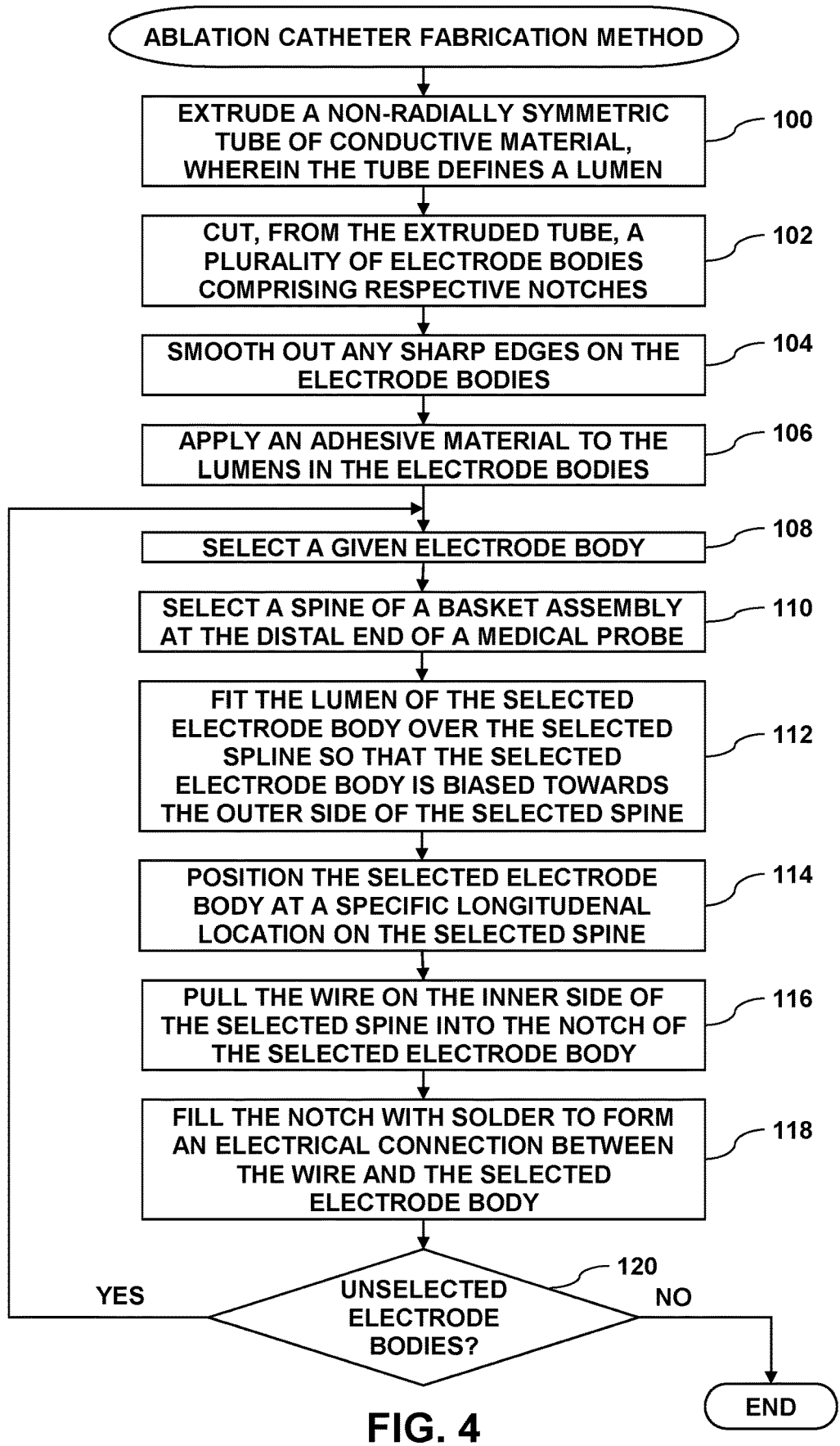
FIG. 4 is a flow diagram that schematically illustrates a method of fabricating the biased electrodes and fitting the biased electrodes to spines of the basket assembly, in accordance with an embodiment of the present invention.
Figure 5A:
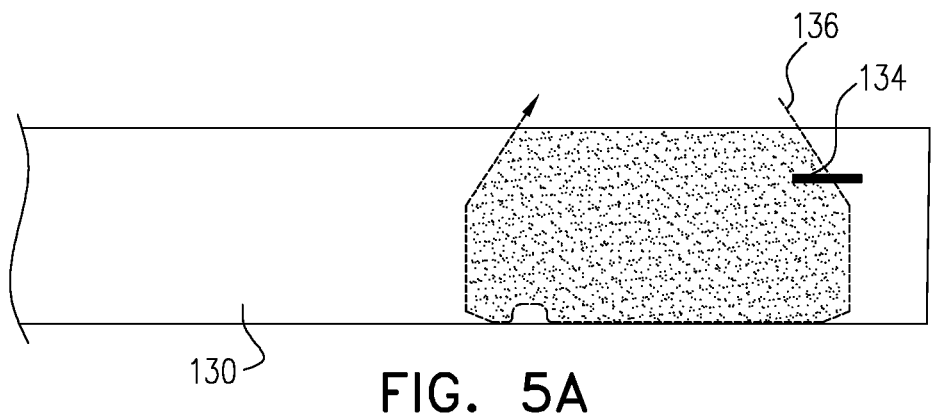
FIGS. 5A-5C, also referred to herein collectively as FIG. 5 are schematic pictorial illustrations showing the fabrication of a given biased electrode from an extruded tube of a conductive material, in accordance with an embodiment of the present invention.
Figure 5B:
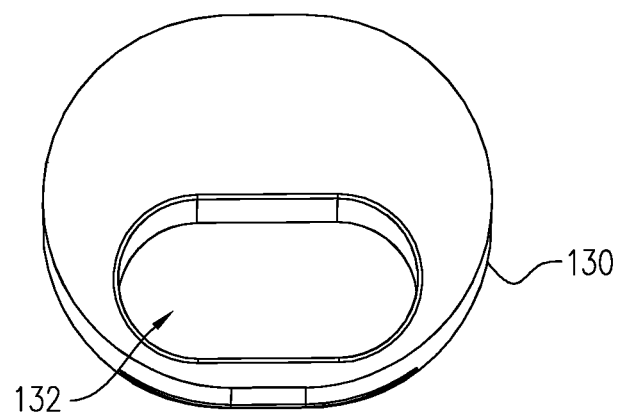
Figure 5C:
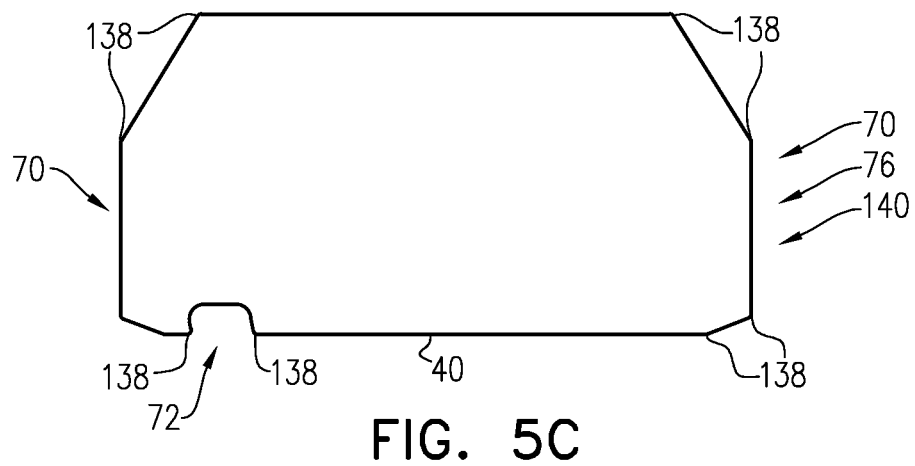

FIG. 4 is a flow diagram that schematically illustrates a method of fabricating electrodes 40 and fitting the electrodes to spines 82, and FIGS. 5A-5C, also referred to herein collectively as FIG. 5, are schematic pictorial illustrations showing the fabrication of a given electrode 40 from an extruded tube 130 of a conductive material, in accordance with an embodiment of the present invention. FIG. 5A shows a longitudinal view of extruded tube 130, FIG. 5B shows a cross-sectional latitudinal view of the tube 130 that defines a tube lumen 132, and FIG. 5C shows a longitudinal view of a given extruded electrode body 40.

In an extrusion step 100, a manufacturer (not shown) extrudes non-radially symmetric tube 130 of conductive material, as shown in the cross-sectional latitudinal view of the tube in FIG. 5B. For example, tube 130 may have a height of 0.04 inches (±0.003 inches) and a width of 0.048 inches (±0.003 inches), the lumen may have a height of 0.017 inches (±0.001 inches) and a width of 0.032 inches (±0.002 inches), the thickness of the conductive material below the lumen may be 0.003 inches (±0.001 inches), and the thickness of the conductive material above the lumen may be approximately 0.02 inches.

In a fabrication step 102, the manufacturer uses a cutting instrument to cut a plurality of electrode bodies 40 (FIG. 5C) from tube 130. In some embodiments, each electrode may have a length of approximately 0.08 inches.

In the example shown in FIG. 5A, the manufacturer can use a cutting instrument such as an electrical discharging machining (EDM) wire 134 to fabricate the electrode bodies from tube 130. In some embodiments, the manufacturer can use EDM wire 134 to fabricate each of the electrode bodies (including notch 72) in a single cutting operation, as shown by a cutting path 136.

Fabrication step 102 may create sharp edges 138 (FIG. 5C) on electrode bodies 40. If medical system 20 is used for performing high-energy ablation procedures such as IRE ablation, applying the high ablation energy to electrodes 40 may result in arcing from edges 138.

In a smoothing step 104, the manufacturer smooths out edges 138 on the fabricated electrode bodies. Examples of smoothing processes that the manufacturer can use include, but are not limited to, tumbling/rumbling and barreling.

In an application step 106, the manufacturer applies an adhesive 140 to inner surfaces 76 of electrode bodies 40.

In a first selection step 108, the manufacturer selects a given fabricated electrode body 40, and in a second selection step 110, the manufacturer selects a given spine 82 for the selected electrode body.

In a fitting step 112, the manufacturer fits the lumen of selected electrode body to the selected spine so that the selected electrode body is biased toward the outer side of the selected spine.

Figure 6:
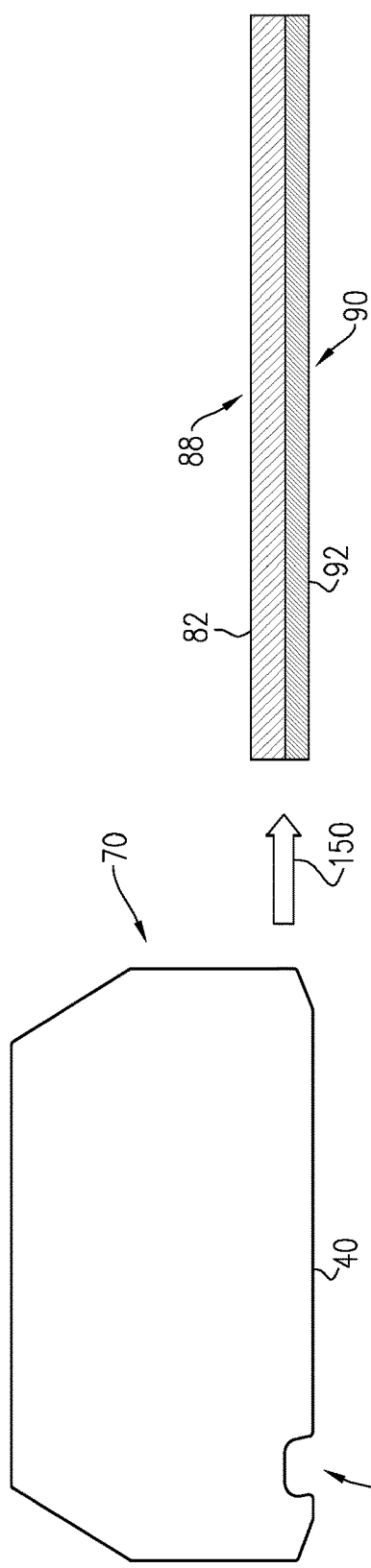
FIGS. 6 and 7 are longitudinal views of fitting the lumen of a given electrode body on a given spine so that the given electrode body is biased toward an outer side of the given spine, in accordance with an embodiment of the present invention.
Figure 7:
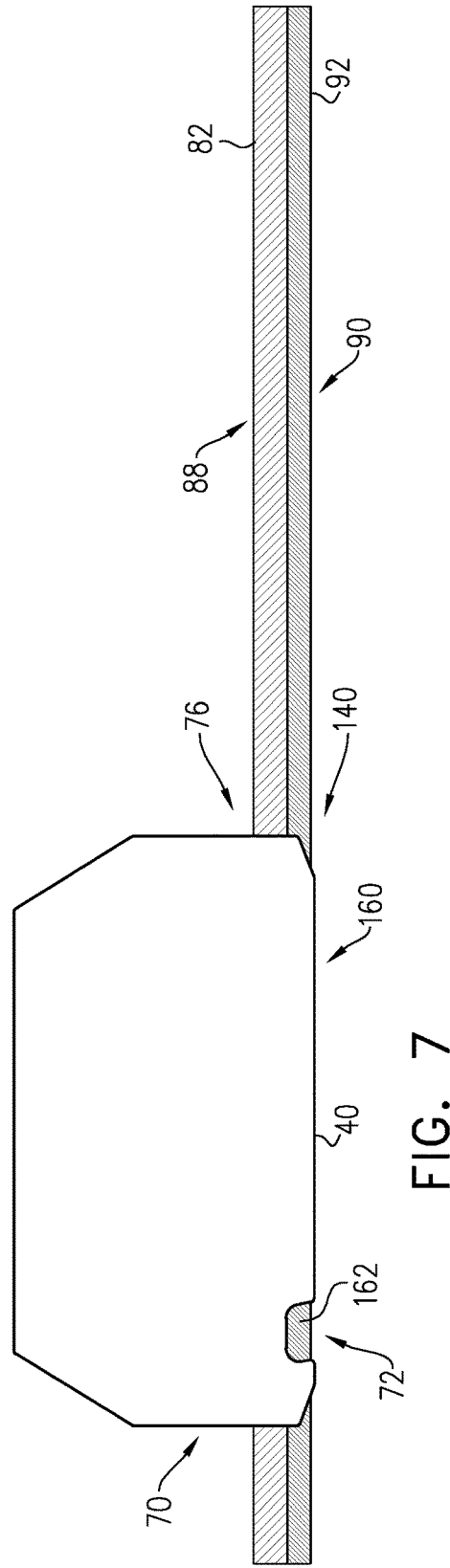

FIGS. 6 and 7 are longitudinal views of fitting lumen 70 of a given electrode body 40 on a given spine 82 (as indicated by an arrow 150 in FIG. 6), so that the given electrode body is biased toward outer side 88 of the given spine, in accordance with an embodiment of the present invention.

In a positioning step 114, the manufacturer positions the selected electrode body at a specific longitudinal location 160 on the selected spine. In some embodiments, positioning the selected electrode body at the desired location enables adhesive 140 to set, thereby forming an adhesive bond between the selected electrode body and the selected spine. One advantage of the configuration of electrodes 40 is that if the adhesive bond breaks between a given electrode 40 and a given spine 82, the lumen of the given spine will still contain the given electrode thereby preventing the given electrode from "breaking off" basket assembly 38.

In a pull step 116, the manufacturer pulls (e.g., "fishhooks") the wire from the inner side of the selected electrode body into the notch of the selected electrode body, and in a connection step 118, the manufacturer fills the notch (i.e., containing the pulled wire) with a solder material 162 (e.g., a gold-tin alloy), thereby forming an electrical connection between the wire and the selected electrode body (and thereby forming an electrical connection between the selected electrode body and ablation module 56).

Finally, in a decision step 120 if there are still any electrode bodies 40 that have not yet been selected for basket assembly 38 (i.e., in step 108), then the method continues with step 108, where the manufacturer can select a previously unselected electrode body 40. The method ends when there are no more unselected electrode bodies 40 for basket assembly 38. For example, the basket assembly shown in FIG. 2 comprises twelve electrodes (i.e., six spines 82 with two electrode bodies fit to each of the spines). Therefore, the method ends upon completing to fix two electrodes to each spine 82.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
providing a medical probe having a plurality of spines;
providing an extruded tube of a conductive material;
performing a cutting operation on the extruded tube so as to form an electrode body; and
fitting the formed electrode body around a given spine.

2. The method according to claim 1, wherein the plurality of spines forms a basket assembly at a distal end of the medical probe.

3. The method according to claim 1, wherein the cutting operation forms sharp edges on the electrode body, and further comprising smoothing out the sharp edges.

4. The method according to claim 1, wherein the extruded tube defines a lumen, and wherein the tube is not radially symmetric about the lumen.

5. The method according to claim 1, wherein the given spine has an outer side and an inner side, and wherein fitting the formed electrode body on the given spine comprises biasing the electrode body towards the outer side of the given spine.

6. The method according to claim 1, wherein the given spine has an outer side and an inner side, and wherein the cutting operation comprises cutting a notch between a lumen of the extruded tube and the inner side of the given spine.

7. The method according to claim 6, wherein the given spine comprises a wire affixed to the inner side of the given spine, and further comprising filling the notch with solder so as to form an electrical connection between the wire and the electrode body.

8. The method according to claim 1, wherein fitting the formed electrode body around the given spine comprises forming an adhesive bond between the electrode body and the given spine.

9. The method according to claim 1, and further comprising providing a set of spray ports configured to deliver an irrigation fluid to the electrodes.

10. The method according to claim 1, and further comprising providing a set of spray ports configured to deliver an irrigation fluid between the spines.

\* \* \* \* \*